United States Patent [19]

Tatsuno

[11] Patent Number: 4,940,326
[45] Date of Patent: Jul. 10, 1990

[54] PARTICLE SIZE MEASURING APPARATUS

[75] Inventor: Kyoichi Tatsuno, Yamato, Japan

[73] Assignee: Kabushiki Kaisha Toshiba, Kawasaki, Japan

[21] Appl. No.: 355,827

[22] Filed: May 22, 1989

Related U.S. Application Data

[63] Continuation-in-part of Ser. No. 168,509, Mar. 15, 1988, abandoned.

[30] Foreign Application Priority Data

Mar. 28, 1987 [JP] Japan .................................. 62-74847

[51] Int. Cl.$^5$ ...................... G01N 15/02; G01N 21/49
[52] U.S. Cl. ..................................... 356/336; 356/339
[58] Field of Search ................................ 356/336, 339

[56] References Cited

U.S. PATENT DOCUMENTS

| | | |
|---|---|---|
| 3,476,463 | 11/1969 | Kreuzer et al. |
| 3,960,449 | 6/1976 | Carleton |
| 4,595,291 | 6/1986 | Tatsuno |
| 4,600,302 | 7/1986 | Sage, Jr. ................................ 356/39 |

FOREIGN PATENT DOCUMENTS 0158147 10/1985 European Pat. Off.

OTHER PUBLICATIONS

Applied Optics, vol. 20, No. 5, P879; M. Quintanilla and A. M. de Frutos, "Holographic Filter that Transforms a Gaussian into a Uniform Beam".

"Determination of Droplet Sizes and Wetness Fraction in Two-Phase Flows Using a Light-Scattering Technique (High Pressure Live Steam of Nuclear Power Plants, Low Pressure Steam Turbines, Cooling Tower Plumes", J. Mech. Eng. Sci.; A. Ederhof; (1976).

Primary Examiner—Davis L. Willis
Assistant Examiner—Matthew W. Koren
Attorney, Agent, or Firm—Oblon, Spivak, McClelland, Maier & Neustadt

[57] ABSTRACT

An optical system for irradiation comprising a light source, a lens, an optical fiber, a rectangular waveguide, an objective lens and a prism and an optical system for receiving light comprising an objective lens, an aperture and an optical fiber are arranged with their optical axes intersecting one another at a point P in a measuring volume. In the optical system for irradiation, the light emitted from the optical fiber and having an intensity distribution expressed by a normal distribution curve is changed to a light having a uniform intensity distribution and a rectangular cross section, which is irradiated through the prism to the point p in the measuring volume. A light scattered at an angle of 90° by a particle flowing through the measuring volume is guided through the optical system for receiving light to a photodetector which converts the scattered light to an electric signal (current) called a scattered light pulse. An arithmetic unit calculates the particle size from the height of this scatterd light pulse and the flow speed from the pulse width.

22 Claims, 6 Drawing Sheets

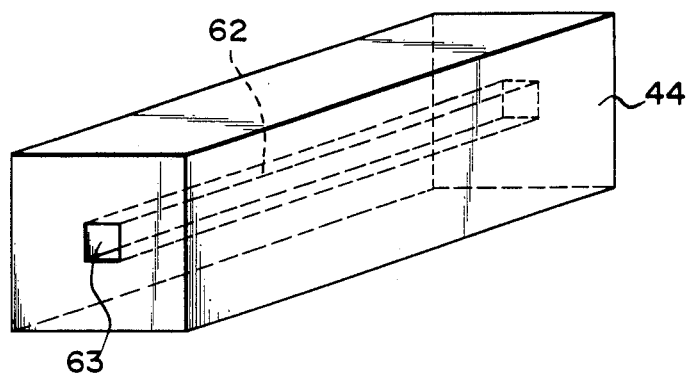
F I G. 8

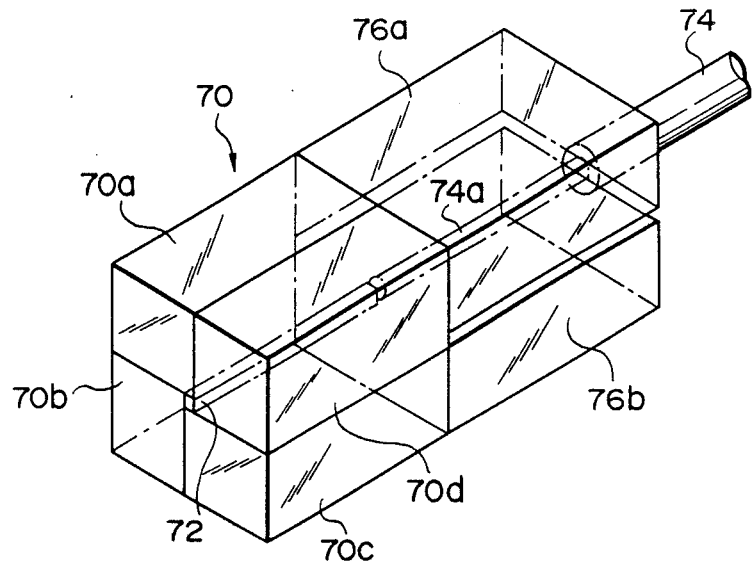
F I G. 9
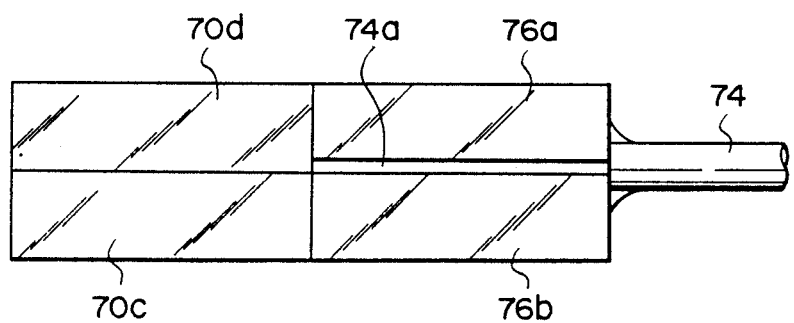
F I G. 10

PARTICLE SIZE MEASURING APPARATUS

This application is a continuation-in-part of application Ser. No. 168,509, filed on Mar. 15, 1988, now abandoned.

BACKGROUND OF THE INVENTION

1. Field of the Invention

This invention relates to a particle size measuring apparatus for optically measuring the particle size and/or particle size distribution of particles.

2. Description of the Related Art

Among the prior art methods, there is a method measuring light intensity scattered by one particle to be measured. This method is usually called the Coulter counter. A prior particle size measuring apparatus embodying this method is described in A. Ederhof, and G. Bibelius, "Determination of Droplet Sizes and Wetness Fraction in Two-phase-flows Using a Light-scattering Technic", Institution of Mechanical Engineering Journal of Mechanical Engineering Science, 1976, pages 21 to 27. Similar apparatuses have been disclosed in Japanese Patent Disclosure No. 78-13625, 81-58638 and 81-145330.

FIG. 1 shows the particle size measuring apparatus in the above paper. The apparatus includes an optical system for irradiation comprising light source 1, optical fiber 3, aperture 15, and objective lens 5 and an optical system for receiving light comprising objective lens 7, prism 16, aperture 8, and optical fiber 9. The two optical systems are arranged in such a manner that the angle between the optical axes is 90° at the point P. The light emitted from light source 1 and transmitted through optical fiber 3 is irradiated to aperture 15. The image of aperture 15 is formed at the point P by means of objective lens 5. The light scattered at an angle of 90° by a particle existing at the point P is collected by objective lens 7 and turned at an angle of 90° by prism 16. The objective lens 7 forms an image at aperture 8 at the point P.

The scattered light through aperture 8 is guided by optical fiber 9 to photomultiplier 10. The photomultiplier 10 converts the scattered light to the electric current signal. The electric signal thus produced is fed to waveform analyzer 17 where the electric signal proportional to scattered light is inverted to the particle size (diameter). The oscilloscope 18 monitors the electric signal.

As shown schematically in FIG. 2, the point P is, in fact, a cube with some dimensions which are defined by the images of apertures 15 and 8 and constitutes the measuring volume.

When a particle flows through this measuring volume in the direction perpendicular to both the two optical axes of objective lenses 5 and 7, the light scattered by the particle at an angle of 90° is received by the optical system for receiving light and is guided into photomultiplier 10 and is converted into an electric signal.

This electric signal is in a form as shown in FIG. 3. The pulse width corresponds to the flow speed of the particle and the pulse height to the particle size (diameter). To put more specific, the pulse width increases as the the particle flowing speed decreases and the pulse height becomes higher as the particle size increases. Hereafter, this pulse is referred to as the scattered light pulse.

The intensity of the scattered light at an angle of 90° by a particle of a known size can be calculated by Mie's theory or Fraunhofer's diffraction theory. Therefore, if the relationship between particle size and scattered light intensity is obtained by calculation beforehand, it is possible to determine particle sizes from the scattered light pulse height measured by waveform analyzer 17.

In the above prior apparatus, however, the intensity distribution of the irradiated light is in the form of normal distribution since light is irradiated through optical fiber 3 to the measuring volume. Thus, it is difficult to illuminate the measuring volume uniformly. That is to say, the light intensity is higher toward the center of the measuring volume and it decreases toward the peripheral area.

Hence, this prior apparatus has a drawback that the scattered light pulse height varies whether the particle flows the central area or the peripheral area of the measuring volume. The drawback results in errors in particle size measurements.

To avoid this problem, it is necessary to guide particles to be measured via a very thin pipe and finely control the flowing position of the particles so that the particles flow an area (central area) in the measuring volume where the intensity of the projected light is relatively uniform. However, this control itself is no easy matter and if this control is implemented, it is impossible to use the whole area of the measuring volume, and the number of particles that can be measured per unit time decreases notably. Consequently, it takes a long time to obtain particle size. And, to obtain a particle size distribution is virtually impossible.

As described above, with particle size measuring apparatuses of the prior art, measurement errors occur depending on the flowing position of the particles in the measuring field of view. If the flowing position is limited to the central area to solve this problem, long time has to be taken for measurement.

SUMMARY OF THE INVENTION

The object of this invention is to provide a particle size measuring apparatus capable of solving the above-mentioned problem that a long time is taken in measurement if the flowing position of particles is limited to reduce measurement errors that occur depending on the flowing position in the measuring volume and also capable of measuring the size of many particles with high accuracy and in a short time.

According to this invention, a particle size measuring apparatus comprises a light source for emitting a light; a waveguide, provided between the light source and a measuring volume through which a particle is flowed, for converting the light emitted from the light source to a light having a uniform intensity distribution and for irradiating a converted light to the measuring volume; an optical system for receiving a light scattered at a predetermined angle by the particle and for producing a scattered light pulse for each particle; and an arithmetic unit for obtaining the size of the particle based on the scattered light pulse height.

With a particle size measuring apparatus according to this invention, the light irradiated into the measuring volume is in a uniform distribution. There is not much change in the level of the scattered light even if there are changes in the flowing position of particles in the measuring volume, thus assuring high accuracy for particle size measurement.

Further, it is not necessary to limit to a narrow extent the flowing position of the particle and it is possible to feed a large number of particles through the measuring value for a short time by using a thick pipe and supply particles at a high flow speed. As a result, data of particle size distribution can be obtained in a short time.

BRIEF DESCRIPTION OF THE DRAWINGS

FIG. 8 is a view showing another practical example of the rectangular waveguide used in this embodiment.

FIG. 9 is a perspective view showing another modification of a rectangular waveguide according to this invention; and FIG. 10 is a side view of the modification of FIG. 9.

DETAILED DESCRIPTION OF THE PREFERRED EMBODIMENTS

A particle size measuring apparatus as a preferred embodiment of this invention will now be described with reference to the accompanying drawings.

Figure 4:
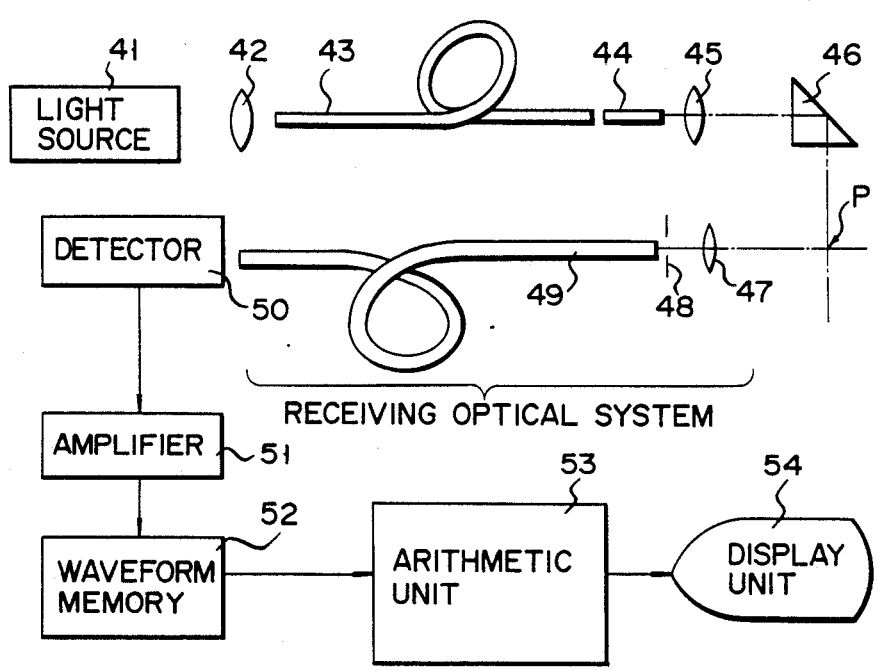
FIG. 4 is a constructional view of a particle size measuring apparatus of an embodiment according to this invention.

Referring to FIG. 4, light source 41 is a laser source, a xenon lamp, a halogen lamp or an LED, for example. The light from this light source 41 is incident to optical fiber 43 through lens 42. Optical fiber 43 is used to guide the light from light source 41 to the neighborhood of a measuring position.

The light emitted from optical fiber 43 is incident to rectangular waveguide 44.

The intensity distribution of the light emitted from optical fiber 43 is a normal distribution. The light intensity is high at the center (at the axis of the optical fiber) and decreases toward the peripheral area. Rectangular waveguide 44 serves to shape the image irradiated from rectangular waveguide 44 into a rectangular form. The light emitted from rectangular waveguide 44 is guided through objective lens 45 and prism 46 to the point P at the measuring position. In this case, objective lens 45 and prism 46 are arranged so that the image of the outlet cross section of rectangular waveguide 44 can be formed at the point P. The optical system for irradiation is formed of light source 41, lens 42, optical fiber 43, rectangular waveguide 44, objective lens 45 and prism 46.

Figure 5:
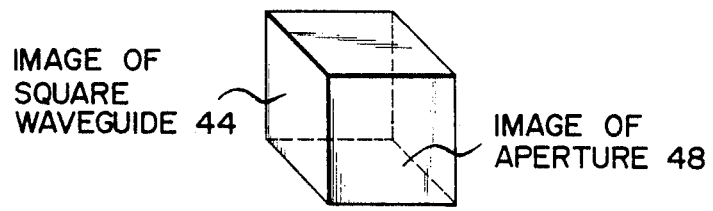
FIG. 5 is a view schematically showing the measuring volume in the embodiment.

On the other hand, the image at the point P is incident through objective lens 47 and aperture 48 to optical fiber 49 by the receiving optical system for receiving light, which is so arranged that its optical axis intersects perpendicularly to the optical axis of the optical system for irradiation at the point P. In this case, objective lens 47 is arranged so that the image of aperture 48 is formed at the point P. Under the above arrangement, a measuring volume defined by the image of the outlet cross section of rectangular waveguide 44 and the image of aperture 48 is formed at the point P as schematically shown in FIG. 5. Aperture 48 may be in any form, but if the flow speed of the particle is to be measured, the cross section of rectangular waveguide 44 must be in a rectangular or square form. If particle size only is measured, the cross section of waveguide 44 need not be in a rectangular or square form, but may be in a circular form.

Figure 1:
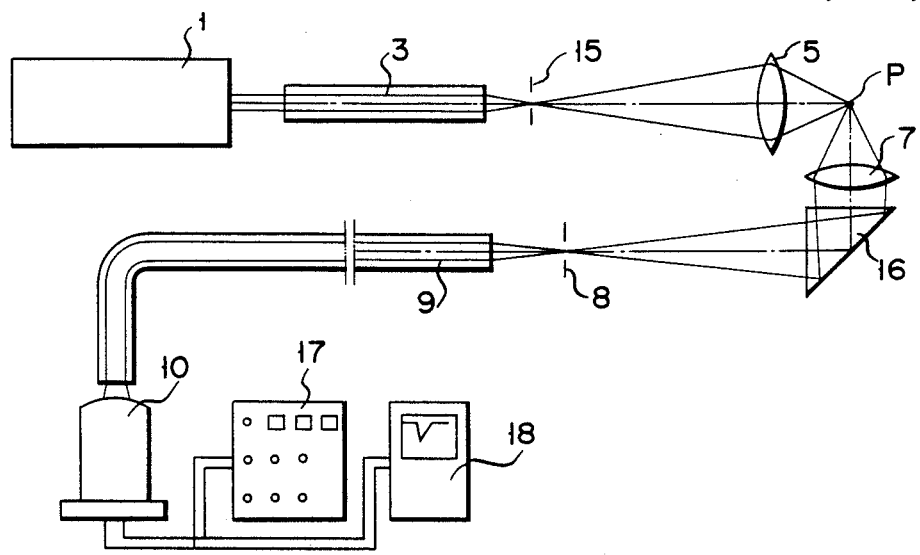
FIG. 1 is a constructional view of a conventional particle size measuring apparatus utilizing the Coulter counter.
Figure 2:
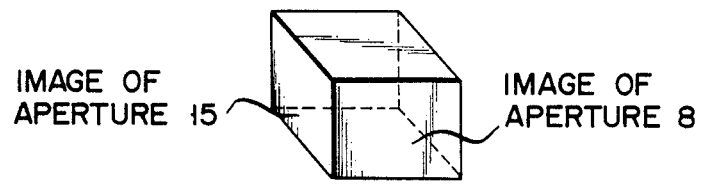
FIG. 2 is a view schematically showing the measuring volume.
Figure 3:
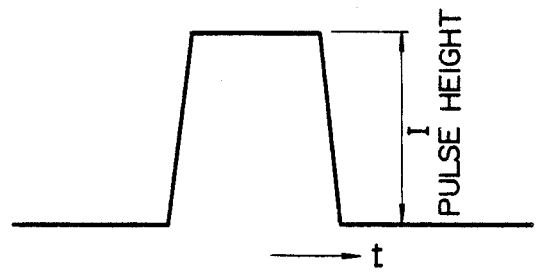
FIG. 3 is a view showing the waveform of a scattered light pulse.

The scattered light in the 90° direction by the particles in this measuring volume is transmitted through objective lens 47, aperture 48 and optical fiber 49 into photodetector 50 such as a photomultiplier whereby the incident scattered light is converted to an electric signal (current) called a scattered light pulse as shown in FIG. 3.

This scattered light pulse is subjected to current-to-voltage conversion in amplifier 51 and amplified therein. The amplified voltage pulse is input to waveform memory device 52. Waveform memory device 52 converts the analog input scattered light pulse to digital data and stores it in a digital memory as a shape of a waveform. The waveforms of scattered light pulses stored in the memory are read by arithmetic unit 53.

The intensity of the scattered light due to a particle with a known particle size can be calculated using Mie's theory or Fraunhofer's diffraction theory.

Figure 6:
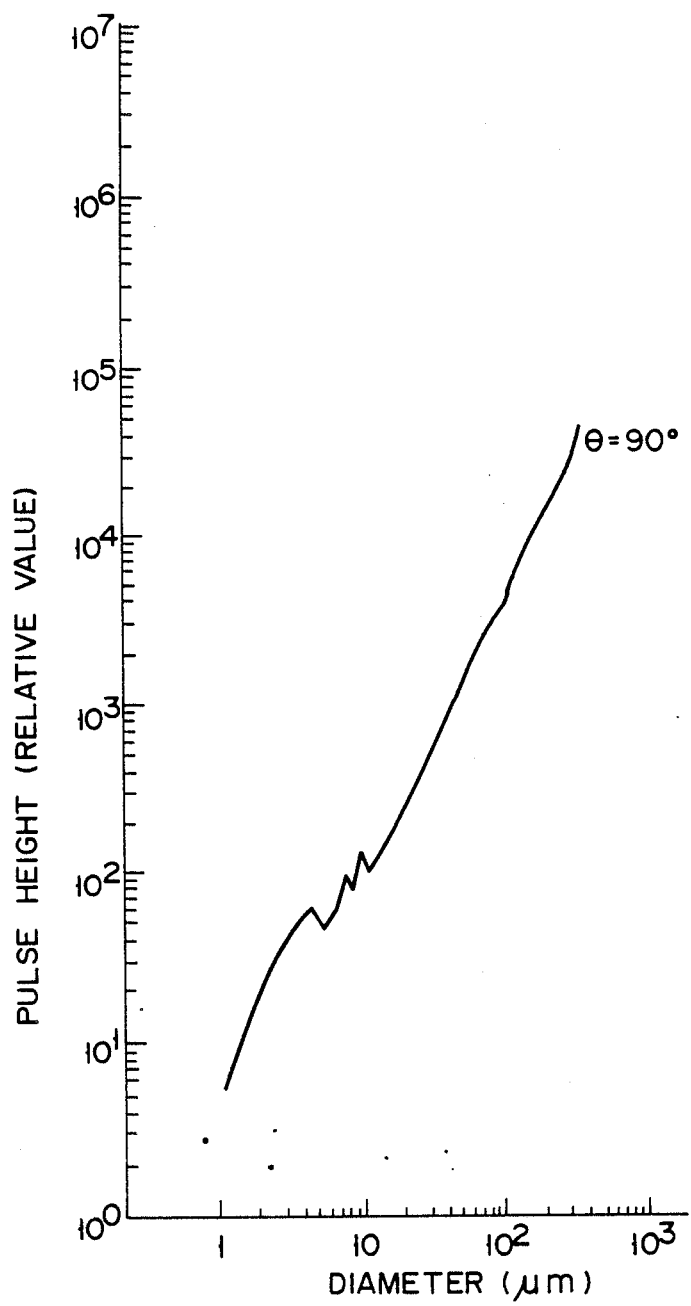
FIG. 6 is a view showing the relationship between the scattered light pulse heights and the size of particles.

FIG. 6 shows the relationship between the size (diameter) of particles being measured that flow through the measuring volume and the pulse height. Using this relationship, the scattered light pulse height is converted to the particle size.

On the basis of the relationship between the size of particles being measured and the scattered light pulse height, arithmetic unit 53 obtains the particle size and speed (width of the scattered light pulse) of many particles. Arithmetic unit 53 obtains particle size distribution and speed distribution from data of particle size and speed obtained and displays the results on display unit 54.

Figure 7:
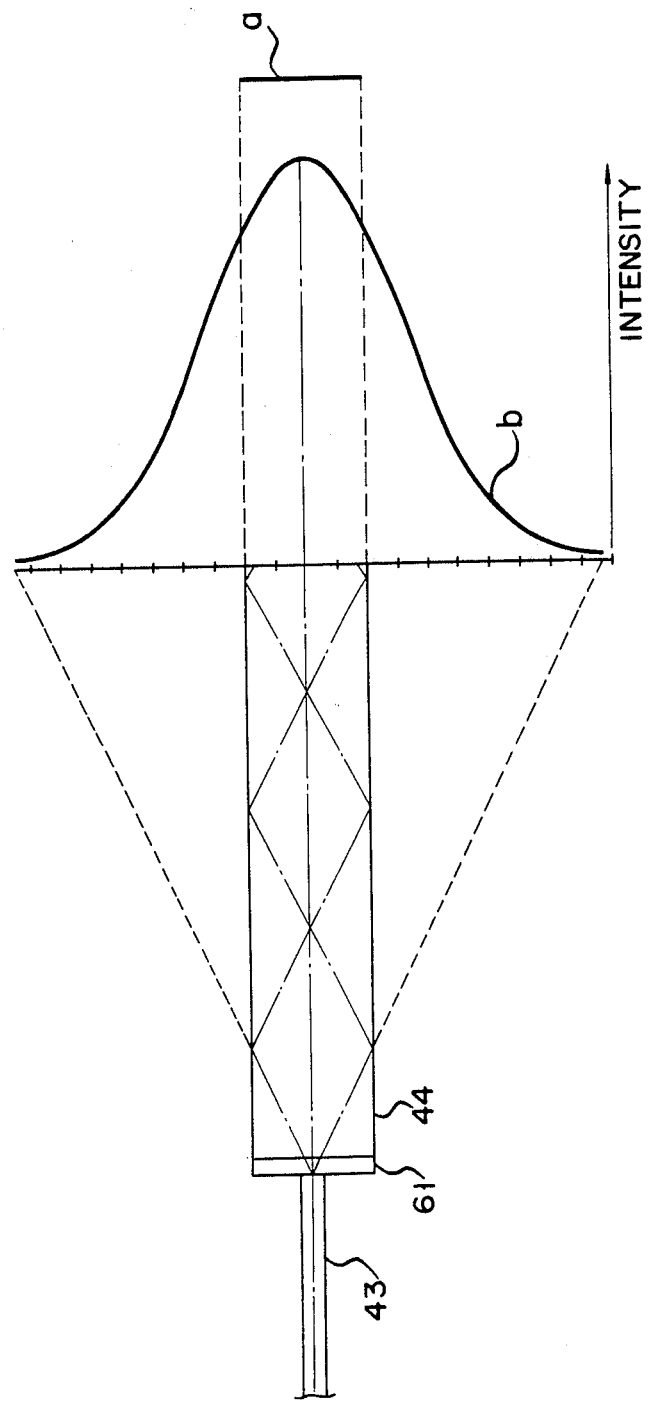
FIG. 7 is a view showing a practical example of a rectangular waveguide used in this embodiment.

Rectangular waveguide 44 is formed of a rectangular rod of transparent glass, for example. As shown in FIG. 7, light emitted from optical fiber 43 is changed into light with a rectangular sectional form by utilizing total reflection at the glass surfaces and the intensity distribution is made uniform as indicated by the characteristic line a. The characteristic line b indicates the intensity distribution (normal distribution) when rectangular waveguide 44 is not used. To be more specific, when the light is incident to rectangular waveguide 44 formed of transparent glass, the light incident into the central portion of the end face of rectangular waveguide 44 reaches the central portion of the measuring volume. However, the light obliquely incident into waveguide 44, is totally reflected and is substantially subjected to a Fourier-transform.

The intensity of the irradiated light in the measuring volume is distributed uniformly as shown in FIG. 7. The longer the length of rectangular waveguide 44, the more uniform the intensity distribution becomes. However, if the irradiation loss is great at objective lens 45, it is difficult to obtain a uniform intensity distribution since the Fourier transformed components of higher order are lost. Therefore, it is desirable to use objective lens 45 of a large aperture.

Then, the scattered light pulse height can be made at almost the same level both when the particle flows the central portion of the measuring volume and when it flows the peripheral area. This improves the accuracy of particle size measurement based on the scattered light pulse height. In addition, since there are fewer variations in the width of the scattered light pulse according to the position where particles flow, the accuracy is improved in particle speed measurement on the basis of pulse width. As this apparatus can be used effectively for measurement in the whole area of the measuring volume, it is possible to flow a large number of particles per unit time and measure a large number of particles in a short time, thereby obtaining particle size distribution and speed distribution quickly.

When a laser source is used for light source 41 of the optical system for irradiation, there is a problem of intensity irregularity due to speckles. This problem can be mitigated by inserting light-scattering member 61 such as a ground glass plate, for example, at the incident end face of rectangular waveguide 44 as shown in FIG. 7. The light-scattering member may be inserted at any position of the emitting optical system. Instead of providing a ground glass plate, the end face of rectangular waveguide 44 may be finished as a ground glass.

This invention is not limited to the preferred embodiment described above but may be embodied in various forms. For example, with regard to rectangular waveguide 44, it is possible to form rectangular rod-like cavity 62 in the center of waveguide 44 as shown in FIG. 8 and attach mirrors 63 or light-reflecting film on the four internal surfaces of this cavity 62.

Though the configuration of FIG. 4 is such that the light scattered at an angle of 90° is used for measurement, the scattering angle is not limited to 90°. If the scattering angle is decreased, the scattered light pulse height can be increased and the signal-to-noise ratio in measurement can be improved. Conversely, if the scattering angle is increased to be greater than 90° to measure backward scattered light, the measuring system can be reduced in size. In short, the optimal scattering angle has only to be selected according to the purpose and conditions such as the arranged position of a measuring apparatus.

In the above embodiment, the particle size measuring apparatus is so arranged as to measure the flow speed as well as the size of particles. Needless to say, however, this invention can be applied to equipment for measuring particle size only. When particle size only is measured, a pulse height analyzer may be used in place of waveform memory device 52 and arithmetic unit 53.

Another modification of a rectangular waveguide according to the present invention will be now described.

FIG. 9 is a perspective view showing this modification. In the embodiment shown in FIG. 4, rectangular waveguide 44 is arranged separate from optical fiber 43. On the other hand, in the modification shown in FIG. 9, rectangular waveguide 70 is arranged so as to be in contact with optical fiber 74, thus improving the precision in making them coaxial with each other. Rectangular waveguide 70 is comprised of four rectangular prisms 70a, 70b, 70c, and 70d, all made of synthetic quartz and having rectangular cross sections and rectangular prism 72 made of synthetic quartz and having an approximately 0.2 mm square cross section. These prisms 70a–70d are connected by an epoxy type bonding material so that waveguide 70 as formed has, in its center portion, a prism-shaped channel extending therethrough having an approximately 0.2 mm square cross section. Rectangular prism 72 is inserted into this channel and is connected to prisms 70a–70d by an epoxy type bonding material. The boundary between prism 72 and prisms 70a–70d which is the bonding material acts as a total reflecting surface if the reflective indexes of the bounding material and prism 72 are set so as to satisfy the condition of total reflection. In this modification, the reflective index $n_a$ of the bonding material is 1.394 and that $n_g$ of prism 72 is 1.45. The numerical aperture (N.A.) of the rectangular waveguide is $\sin \theta = \sqrt{n_g^2 - n_a^2} = 0.4$. The N.A. of optical fiber 74 is a little smaller than that of waveguide 70. Therefore, while a light is being transmitted through channel 72, the light is rendered so as to have a uniform intensity distribution.

Further, it is possible to omit using the bonding material between prism 72 and prisms 70a–70d if the diameter of prism 72 is exactly the same as that of channel formed in the center portion of prisms 70a–70d. In this case, the boundary between prism 72 and prisms 70a–70d acts as a total reflecting surface if the reflective indexes of the prisms 70a–70d and prism 72 are set so as to satisfy the condition of total reflection.

The front end of optical fiber 74 is connected to the rear end of rectangular waveguide 70. More accurately, the covering overlapping the front end portion of optical fiber 74 is removed, thus unwrapping body 74a of the optical fiber. Body 74a is arranged to be clamped by two prisms 76a and 76b, and those prisms are bonded together with a bonding material. The front ends of prisms 76a and 76b are bonded together with the rear end of waveguide 70 by using a bonding material of lens-bond type or of ultraviolet-hardening type. The front end surfaces of prisms 76a and 76b have been subjected to the optical polishing process. As described above, waveguide 70 and optical fiber 74 can be stably combined with each other. As a result, optical fiber 74 and waveguide 70 can be kept coaxial with each other. FIG. 10 is a side view of this modification.

Thus, according to the modification of the present invention, the following advantages can be attained:

1. The waveguide 70 has light guide prism 72 with a small cross section and a measuring volume is formed by enlarging the cross section of the light beam emitted from prism 72 by an optical system 45. This enables the distance between the the optical system 45 and the measuring volume to be increased, as a result of which the probe is free from the restriction of its location.

2. For the reason that the size of the lens 45 is subjected to restriction, it is preferable to reduce the N.A. of the waveguide 70 as much as possible. If the N.A. is large, the light radiated from the optical fiber 74 will be scattered, resulting in that accurate image-formation cannot be performed, and that the measuring volume cannot be formed so as to be exactly square. In this modification, the value of the N.A. is controlled by controlling the refractive index $n_g$ of the bonding material.

As set forth above, according to this invention, it is possible to make uniform the intensity distribution of the irradiated light in the measuring volume by providing a waveguide in the optical system for irradiation, thereby substantially increasing the measuring accuracy of particle size and obtaining a particle size distribution curve in a short time.

What is claimed is:

1. An apparatus for measuring a size of a particle flowing through a measuring volume, comprising:
   light source means for emitting a light;

irradiating means, provided between said light source means and the measuring volume, for converting the light emitted from said light source means to a light having a uniform intensity distribution and for irradiating a converted light to the measuring volume, said irradiating means comprising an optical fiber for leading the light emitted from said light source means to the measuring volume, a waveguide member connected to a front end of said optical fiber for transmitting the light emitted from said optical fiber by way of total reflection from the walls thereof, and support means for fixedly supporting a front portion of the optical fiber to align the optical fiber and the waveguide member in a coaxial manner;

light-receiving means for receiving a light irradiated from said irradiating means and scattered to a predetermined angle by the particle and for producing a scattered light pulse for each particle; and means for obtaining the size of the particle based on a scattered light pulse height.

2. An apparatus according to claim 1, wherein said irradiating means comprises a waveguide into which the light emitted from said light source means is introduced, said waveguide being a glass rod which allows the light introduced into a central portion of an incident end face to travel in a straight course and which allows the light introduced into a peripheral area of the incident end face to travel by reflecting repeatedly at a boundary surface separating the glass rod and air.

3. An apparatus according to claim 2, wherein said glass rod comprises a rectangular cross section.

4. An apparatus according to claim 1, wherein said irradiating means comprises a waveguide into which the light emitted from said light source means is introduced, said waveguide being a rod-like member having a rod-like cavity in a central portion of said waveguide and a light-reflecting member arranged on a circumferential surface of the cavity, said waveguide allows the light introduced into a central portion of an incident end face to travel in a straight course and allows the light introduced into a peripheral area of the incident end face to travel by reflecting repeatedly at a boundary surface separating the glass rod and air.

5. An apparatus according to claim 4, wherein said rod-like cavity comprises a rectangular cross section.

6. An apparatus according to claim 1, wherein said light source means comprises means for emitting a coherent light and said irradiating means comprises means for reducing the coherency of said coherent light.

7. An apparatus according to claim 6, wherein said coherency reducing means comprises a ground glass.

8. An apparatus according to claim 1, wherein said means for obtaining the particle size comprises a wave height analyzer.

9. An apparatus according to claim 1, further comprising means for obtaining a flowing speed of said particle from a width of said scattered light pulse.

10. An apparatus according to claim 9, wherein said means for obtaining the speed of a particle are a waveform memory device and an arithmetic unit.

11. An apparatus according to claim 1, wherein said support means is formed of two prism members having rectangular cross sections, said prism members being connected to each other by a bonding material so that they clamp the front portion of said optical fiber, and said waveguide member is formed of four prism members having rectangular cross sections, said four prism members being connected to said two prism members of said support means and being connected to one another by the bonding material so that the channel having a square cross section is defined thereby, the channel being filled with an auxiliary prism member which has a square cross section and is connected to the four prism members by the bonding material.

12. An apparatus according to claim 11, wherein the prism members of said support means and the prism members of said waveguide member are made of synthetic quartz, and said bonding material is of an epoxy-type.

13. An apparatus according to claim 12, wherein the refractive index of said synthetic quartz is equal to 1.45, and the refractive index of said bonding material is equal to 1.394.

14. An apparatus according to claim 13, wherein the numerical aperture of said optical fiber is greater than that of said waveguide member.

15. An apparatus according to claim 12, wherein said support means and said waveguide member are connected to each other by a bonding material of lens-bond type or of ultraviolet-hardening type.

16. A particle detecting apparatus comprising:
light source means for emitting a light;
waveguide means for converting the light from said light source means to a light having a uniform intensity distribution, said irradiating means comprising an optical fiber for leading the light emitted from said light source means to the measuring volume, a waveguide member connected to a front end of said optical fiber for transmitting the light emitted from said optical fiber by way of total reflection from the walls thereof, and support means for fixedly supporting a front portion of the optical fiber to align the optical fiber and the waveguide member in a coaxial manner;
first objective lens means for forming an image of an outlet end face of said waveguide means on a point;
second objective lens means for collecting the light from said point;
aperture means where an image of said point is formed by said second objective lens means;
means for receiving the light from said aperture means; and
means for detecting the presence of a particle on said point from an output of said receiving means.

17. An apparatus according to claim 16, wherein said waveguide means comprises a waveguide which allows the light introduced into a central portion of an incident end face to travel in a straight course and which allows the light introduced into a peripheral area of the incident end face to travel by reflecting repeatedly at a boundary surface separating the glass rod and air.

18. An apparatus according to claim 16, wherein said detecting means comprises means for measuring a size of the particle at said point from the output of said receiving means.

19. An apparatus according to claim 16, wherein said detecting means comprises means for measuring the speed of the particle flowing past said point from the output of said receiving means.

20. An apparatus according to claim 16, wherein said waveguide means comprises first optical fiber means for transmitting the light from said light source and a waveguide for making an intensity distribution of the light transmitted through said first optical fiber means uniform, said first objective lens means comprises a first objective lens and a prism for turning, at an angle of 90°, the optical path of the first objective lens, said second objective lens means comprises a second objective lens with the optical axis intersecting the optical axis of said prism at an angle of 90° on said point, and said receiving means comprises a second optical fiber for transmitting the light from said aperture means along said second optical fiber to a detector which receives transmitted light.

21. An apparatus according to claim 20, further comprising a light-scattering plate provided between said first optical fiber means and said waveguide channel.

22. An apparatus according to claim 16, wherein said waveguide means comprises a waveguide being a rod-like member having a rod-like cavity in a central portion of said waveguide and a light-reflecting member arranged on a circumferential surface of the cavity, said waveguide allows the light introduced into a central portion of an incident end face to travel in a straight course and which allows the light introduced into a peripheral area of the incident end face to travel by reflecting repeatedly at a boundary surface separating the glass rod and air.

* * * * *